United States Patent [19]
Yakabe et al.

[11] Patent Number: 5,393,378
[45] Date of Patent: Feb. 28, 1995

[54] METHOD FOR MEASURING AND CONTROLLING FIBER VARIATIONS IN PAPER SHEET

[75] Inventors: Masahiro Yakabe, Narita; Satoshi Suzuki, Tokyo; Sadao Degawa, Komae; Shigeki Murayama, Yokohama; Koichi Ishibashi, Tokyo; Ikuo Nakashima, Sayama; Koji Sakai, Kawasaki, all of Japan

[73] Assignee: Ishikawajima-Harima Jukogyo Kabushiki Kaishi, Tokyo, Japan

[21] Appl. No.: 25,726

[22] Filed: Mar. 2, 1993

Related U.S. Application Data

[63] Continuation-in-part of Ser. No. 640,409, Jan. 23, 1991, abandoned.

[30] Foreign Application Priority Data

| | | | |
|---|---|---|---|
| May 31, 1989 | [JP] | Japan | 1-138439 |
| Jul. 7, 1989 | [JP] | Japan | 1-176576 |
| Oct. 17, 1989 | [JP] | Japan | 1-269906 |
| Oct. 17, 1989 | [JP] | Japan | 1-269907 |

[51] Int. Cl.⁶ .................... G01N 21/89; D21F 7/06
[52] U.S. Cl. ...................... 162/61; 162/198; 162/259; 162/263; 364/471; 382/52
[58] Field of Search ............... 162/252, 253, 259, 263, 162/198, 61; 382/52; 364/471

[56] References Cited

U.S. PATENT DOCUMENTS

| | | | |
|---|---|---|---|
| 3,962,719 | 12/1975 | Spitz | 162/253 |
| 4,205,341 | 5/1980 | Mitsuya et al. | 382/52 |
| 4,500,968 | 2/1985 | Bialkowski | 162/252 |
| 4,578,713 | 3/1986 | Tsao et al. | 382/52 |
| 4,831,658 | 5/1989 | Umeda et al. | 382/52 |
| 5,011,573 | 4/1991 | Niemi | 162/259 |

*Primary Examiner*—Steve Alvo

[57] ABSTRACT

A formation control method and apparatus in which an image is emitted from a light source and transmitted through a predetermined area of paper an captured by a camera to be displayed as transmitted light image on a display of an image processing computing element, the transmitted light image displayed on the display being image-analyzed to obtain formation factor for quantification of the formation, J/W ratio and the like being optimized by fuzzy control using membership functions based on said formation factor so as to improve the formation.

10 Claims, 20 Drawing Sheets

FIG. 4(d')

1. AVERAGE VALUE OF PRIMARY VARIANCE $$a_v = \frac{\sum_{k=1}^{N} Vavk}{N}$$

2. SECONDARY VARIANCE (VARIANCE OF PRIMARY VARIANCE)

$$Vav = \frac{\sum_{k=1}^{N}(a_v - Vavk)^2}{N}$$

3. VARIANCE OF AVERAGE VALUE $$Vaav = \frac{\sum_{k=1}^{N}(Cavk - Caav)^2}{N}$$

FIG. 4(d)

1. AVERAGE VALUE OF PRIMARY VARIANCE $$a_v = \frac{\sum_{k=1}^{N} Vavk}{N}$$

2. SECONDARY, VARIANCE (VARIANCE OF PRIMARY VARIANCE)

$$Vav = \frac{\sum_{k=1}^{N}(a_v - Vavk)^2}{N}$$

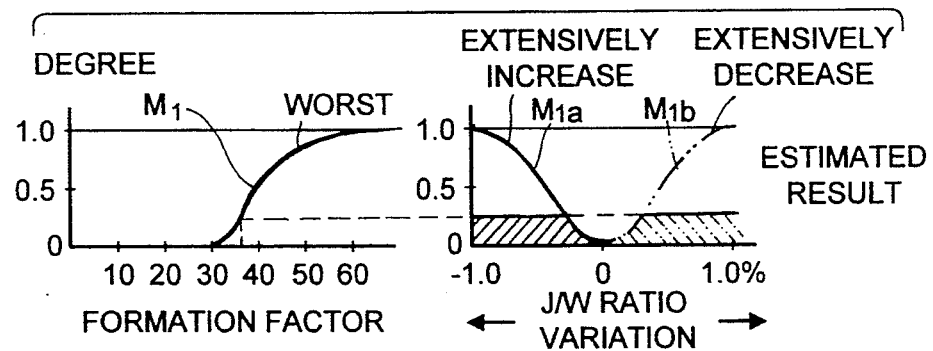
FIG. 14 (I)
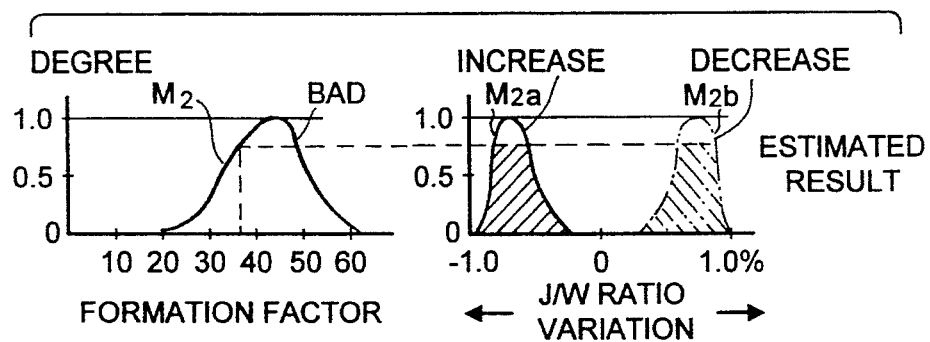
FIG. 14 (II)
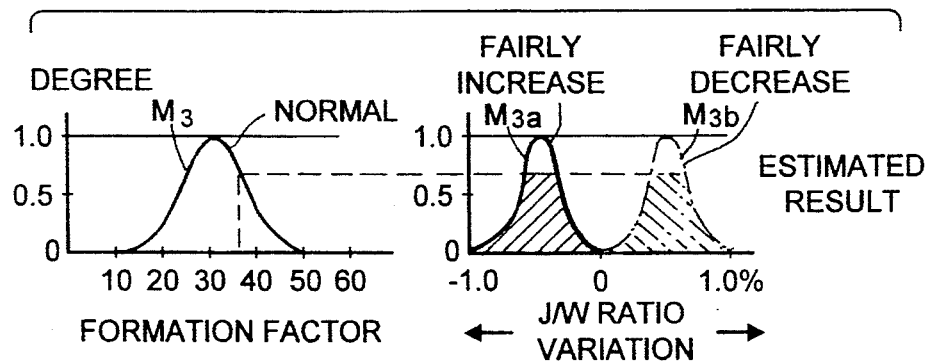
FIG. 14 (III)

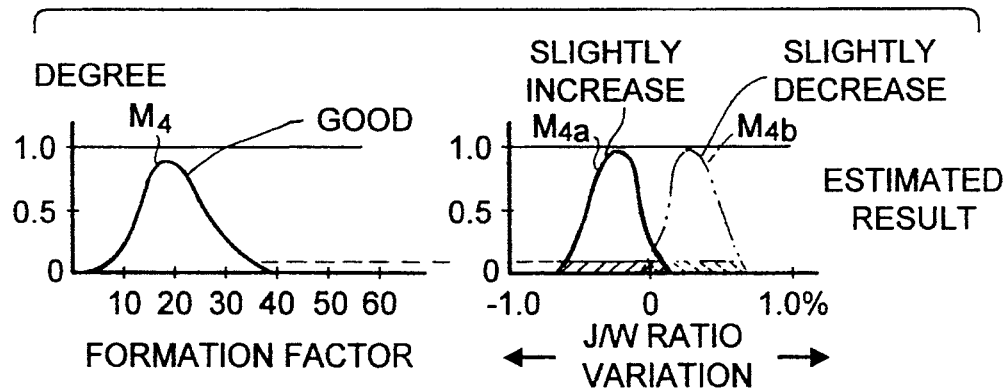
FIG. 14 (IV)
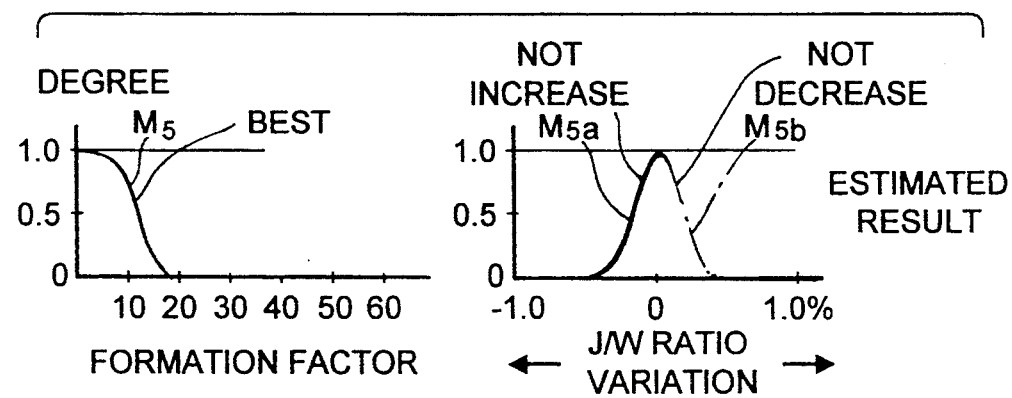
FIG. 14 (V)
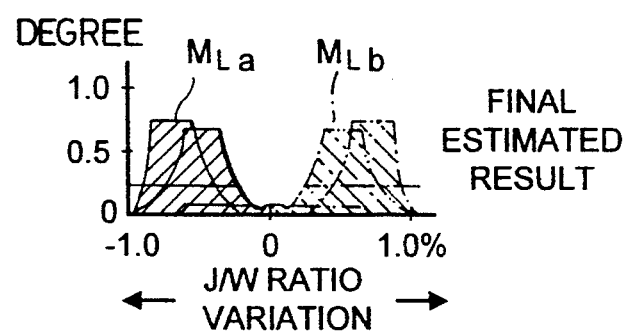
FIG. 14 (VI)

METHOD FOR MEASURING AND CONTROLLING FIBER VARIATIONS IN PAPER SHEET

This application is a continuation-in-part of application Ser. No. 07/640,409, filed Jan. 23, 1991, now abandoned.

TECHNICAL FIELD

The present invention relates to a formation measuring method to identify unevenness of transmitted light on paper as a plane image and to evaluate the property and the quality of the paper so as to control quality improvement and also relates to a formation control method and apparatus using said formation measuring method.

BACKGROUND ART

Quality of paper formation (minute uneven thickness) indicates the degree of fiber variance in paper sheet. The measurement of the degree of fiber variance takes into account the size and distribution of holes, flock distribution, and dust particle measurement. Generally, this has been checked by placing a sample sheet on an inspection box accommodating a light source to visually examine transparency distribution of the sheet.

This method, which is widely used in factories, is rather of subjective nature and results of the inspection varies according to each inspector since sufficient knowledge and long experience are required for such inspection.

For this reason, a formation meter as shown in FIG. 1 has been developed and is practically used. This formation meter comprises upper and lower heads b and c above and below the running paper a to be measured, the lower head c accommodating a light source d such as laser connected to an electric power source and a mirror f for irradiating the light from said light source d onto the paper a. The upper head b accommodates a photocell j for receiving the light e, which has passed through said paper a via a mirror g, a filter h and a lens i.

The light e from the light source d is irradiated on the paper a through the mirror f; the light e passing through the paper a enters the photocell j through a mirror g, a filter h and a lens i and is converted to voltage and is outputted. As shown in FIG. 2, the voltage value is indicated as formation index relative to the time.

When the formation index is measured, jet/wire ratio (J/W ratio) and the like are changed according to said formation index by judgment of an inspector to obtain better formation.

DISCLOSURE OF INVENTION

In the above-mentioned formation meter, however, the diameter of the light e irradiated from the light source d to the paper a is about 1 mm and any fluctuation of transmitted light level is detected as flock size through one-dimensional processing of the transmitted light signal. Although the formation of the paper a is converted to numerical value, the sample for judgment is too small to make total judgment for accurate identification of the formation as judgment through human vision.

In the control of the formation, J/W ratio is adjusted only by trial and error. Because of the control being based on measurement results by the above-mentioned formation meter, which does not necessarily reflect the total conditions, improvement of the paper quality is rather difficult.

The present invention was made to overcome such disadvantages of the prior art and will provide a formation measuring method for more accurate evaluation of the formation objectively not as point but as plane. The present invention will further provide a formation controlling method and apparatus for efficient improvement of paper quality according to results of measurement by the formation measuring method.

BRIEF DESCRIPTION OF THE DRAWINGS

FIGS. 4(a), 4(b), 4(c), 4(d) and 4(d') are views to explain the image processing on a display unit;

FIGS. 14(i), 14(ii), 14(iii), 14(iv), 14(v) and 14(vi) are to explain the procedure to determine the change of J/W ratio according to the formation factors;

BEST MODE FOR CARRYING OUT THE INVENTION

In the following, embodiments of the present invention will be described in connection with the drawings.

Figure 1:
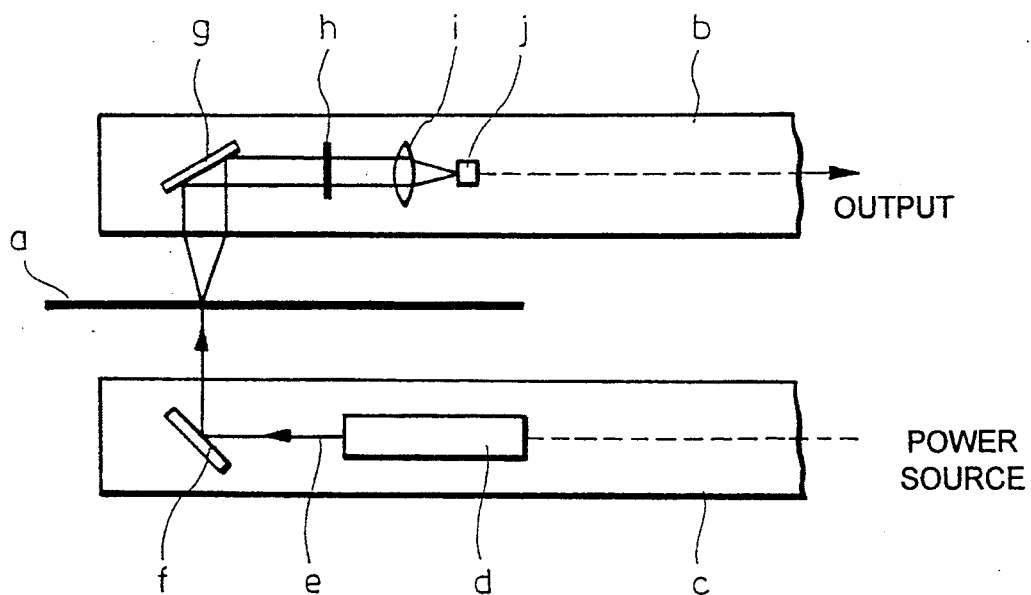
FIG. 1 is a view showing an example of conventional formation meters.
Figure 2:
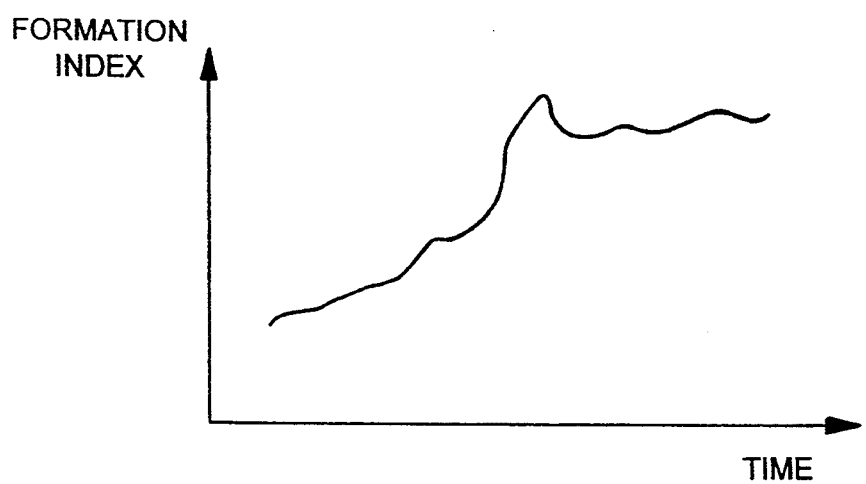
FIG. 2 is a diagram showing the relationship between time and formation index as obtained by the formation meter in FIG. 1.
Figure 3:
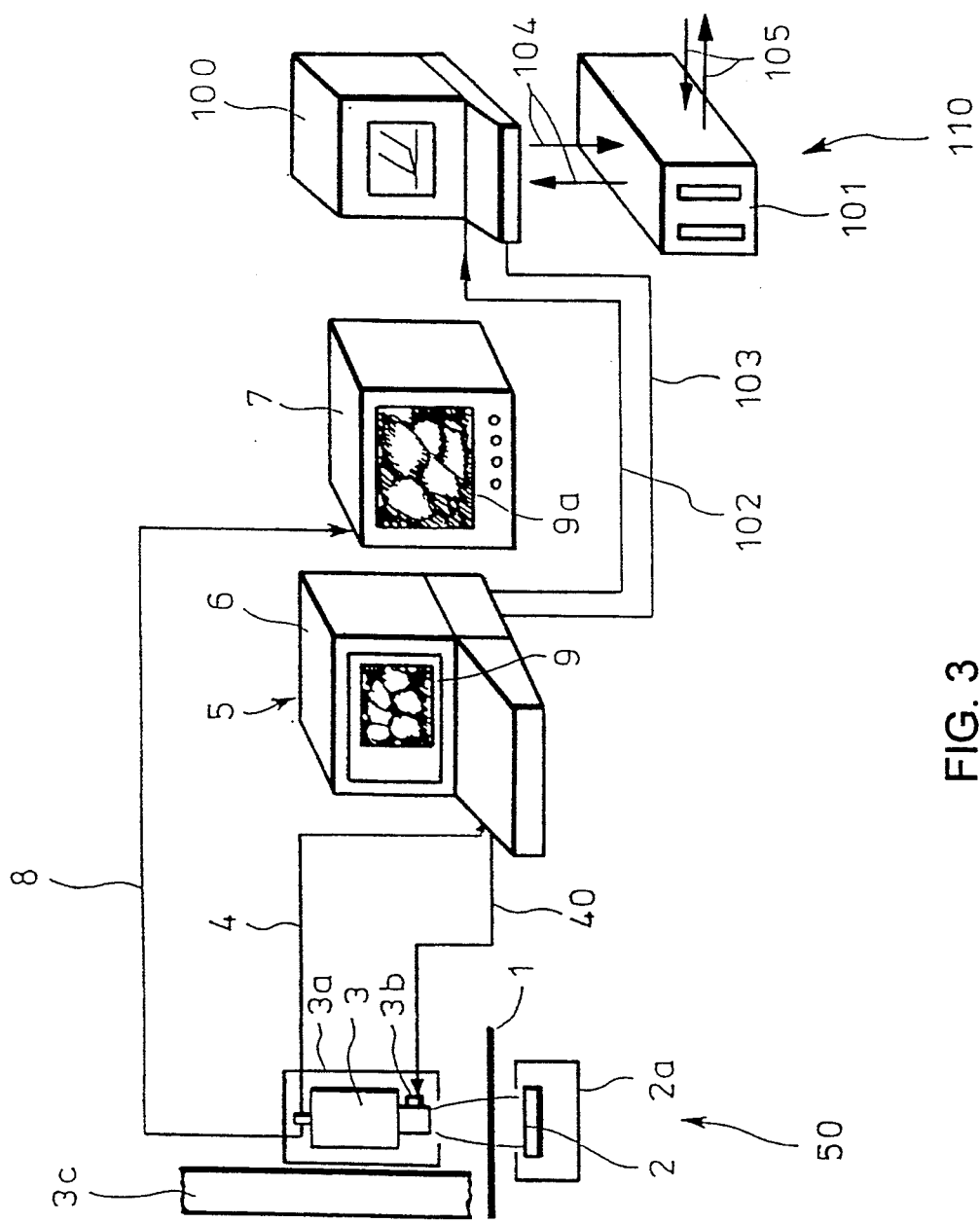
FIG. 3 shows an embodiment of an apparatus for carrying out the formation measuring method of the present invention as well as the formation controlling method using said formation measuring method.
Figure 4A:
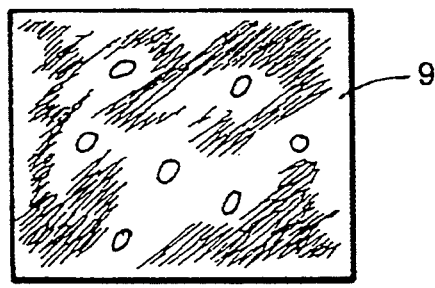
Figure 4B:
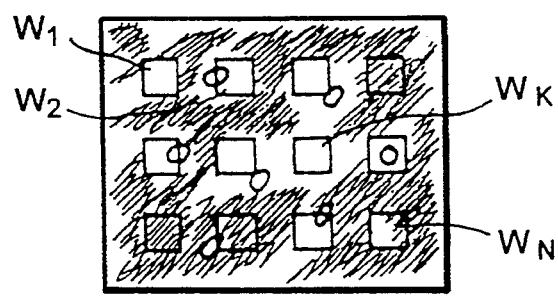
Figure 4C:
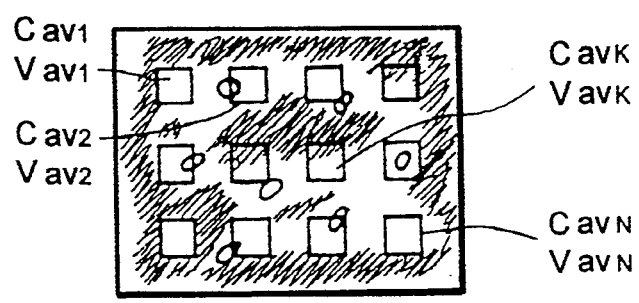
Figure 5:
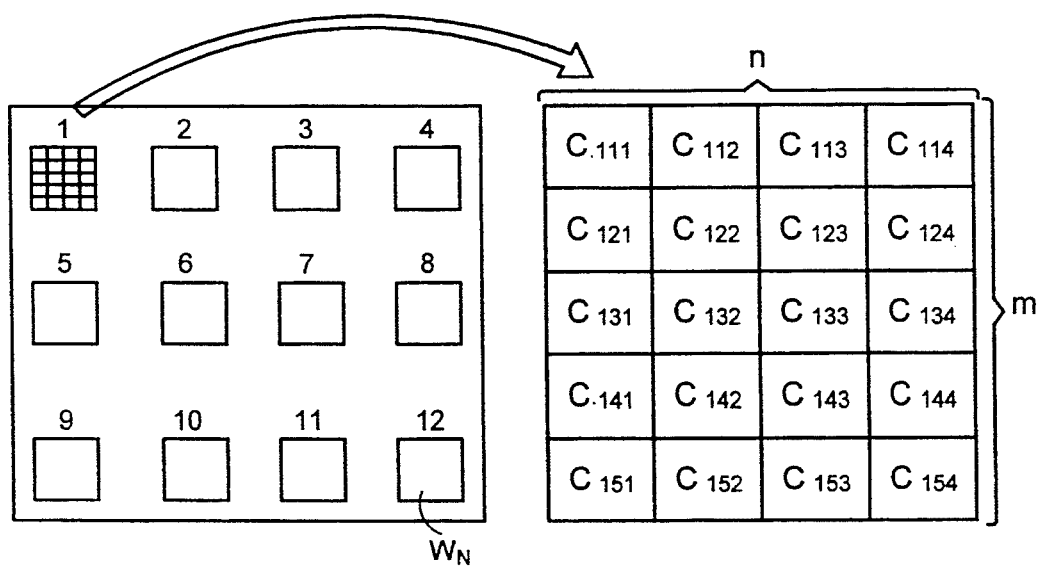
FIG. 5 is a schematic illustration of the relationship between windows and pixels on the display unit.

FIGS. 3, 4 and 5 show an embodiment of the present invention in which disposed on one side of the paper 1 to be measured is a light source box 2a accommodating a light source 2 such as source of parallel beams having variable light quantity. Arranged on its opposite side is a camera box 3a which is movable in widthwise and vertical directions of the paper 1 relative to the rail 3c. The camera box 3a accommodates a camera 3 having zooming function and with an automatic aperture control device 3b to make up a formation meter 50. A CCD (charge coupled device) frame accumulation mode camera or its equivalent is used as camera 3 of this embodiment in combination with a stroboscope 2. The camera 3 is connected through a cable 4 with a computing element 5 for image processing having a display unit 6. The camera 3 is further connected with another display unit 7 through a cable 8 so as to permanently display transmitted light image of the paper 1. The computing element 5 for image processing is connected with the automatic aperture control device 3b through a cable 40 so that a control signal from the image processing computing element 5 is inputted to the automatic aperture control device 3b to perform automatic control of the aperture.

To the image processing computing element 5, a fuzzy control device 110 comprising a control computer 100 and a controller 101 for control is arranged for the controlling purpose. The image processing computer element 5 is connected with the control computer 100 through a formation signal line 102 and a control signal line 103. The computer 100 is connected with the controller 101 through communication lines 104. Further, connected with the controller 101 through the control signal lines 105 are an actuator for changing a ratio of the speed of jet injected from a below-mentioned head box 10 in FIG. 13 to the wire speeds of bottom and top wires 12 and 16, an actuator for changing the angle of foils 14 and the like.

Since the paper 1 to be inspected is of considerable size, a portion of the paper to be picked up by the camera 3 as sample (10 mm × 10 mm or more) is to represent all features of the paper 1 and include an apparent steady area or area where quality of the entire paper 1 can be judged by inspecting this area.

During measurement, adjustment is made such that an adequate quantity of transmitted light is obtained from the light source 2 according to the thickness of the paper 1. As to adjustment of aperture of the camera 3, description will be given later. A signal representative an image entering the camera 3 enters the display unit 7 and forms an image 9a of transmitted light on the paper 1. On the other hand, the image signal entering the image processing computing element 5 is displayed on the display unit 6 as an image 9 in FIG. 4(a) showing an area by which the quality of the entire paper 1 is determinable. On the screen, the concentration of holes and the like is displayed thinner (lighter) than average and overweighted portions with dust and the like attached thereto are displayed denser (darker) than the average.

On the image 9, a predetermined number of windows $W_1, W_2, \ldots, W_k, \ldots, W_N$ are set which have an area by about two times as large as the average size of hole or the minimum size of flock peculiar to paper as a variance calculation unit (FIG. 4(b)). The size and number of the windows can be selected according to the grade, furnish or the like of paper.

Pixels of the display unit 6 may be contained by the quantity of $M = n \times m$ ($n = 4$ and $m = 5$ in the example shown) in a window in FIG. 5. The tone density (referred to hereinafter simply as density) of the pixels in line i and row j in the k-th window $W_k$ is expressed by $C_{kij}$. Thus, the average value of density $C_{aVk}$ in k-th window $W_k$ can be calculated as:

$$C_{aVk} = \frac{\sum_{j=1}^{n} \sum_{i=1}^{m} C_{kij}}{M}$$

The variance $V_{aVk}$ of the density in k-th window $W_k$ (hereinafter referred as primary variance), i.e. the variation of density in a window $W_k$ is calculated as (See FIG. 4(c)):

$$V_{aVk} = \frac{\sum_{j=1}^{n} \sum_{i=1}^{m} (C_{aVk} - C_{kij})^2}{M}$$

Further, the average value $a_V$ of primary variance for all windows $W_1, W_2, \ldots, W_k, \ldots, W_N$ is calculated:

$$a_v = \frac{\sum_{k=1}^{N} V_{aVk}}{N}$$

Based on the average value $a_V$ of primary variance of all windows, the variance $V_{aV}$ of primary variance for all windows $W_1, W_2, \ldots, W_k, \ldots, W_N$ (hereinafter referred as secondary variance) is calculated:

$$V_{av} = \frac{\sum_{k=1}^{N} (a_V - V_{aVk})^2}{N}$$

And the results of the calculation are displayed (See FIG. 4 (d)).

The average value $a_V$ of primary variance for all windows expresses the macro variance on the screen. The formation can be quantitatively determined as the formation factor in relatively wide visual field (formation factor in the case where paper is not even, e.g. the paper having serious defect). In the evaluation in the final stage of control where the entire paper is uniform and formation is evaluated by microjudgment, the formation can be quantitatively determined using the variance $V_{aV}$ (secondary variance) of primary variance of density for all windows as the formation factor.

Further, in addition to the average value $a_V$ of primary variance for all windows and to the secondary variance $V_{aV}$ for all windows as a whole, the variance of average value $C_{aVk}$ in the windows $W_1, W_2, \ldots, W_k, \ldots, W_N$ is calculated:

$$C_{aaV} = \frac{\sum_{k=1}^{N} C_{aVk}}{N}$$

$$V_{aaV} = \frac{\sum_{k=1}^{N} (C_{aVk} - C_{aaV})^2}{N}$$

and the results of calculation may be displayed (See FIG. 4 ($d'$)). The variance $V_{aaV}$ of average value of the density for each window expresses variance $V_{aaV}$ of average value of the density for each window expresses macro-variance of light and dark to average density on the screen and can be used as formation factor for quantitative determination of the formation when it is uniform as a whole and density is very uneven.

It is needless to say that in this case formation may be quantitatively determined using a formation factor through combination of $a_V$, $V_{aaV}$ and $V_{aV}$ according to object.

Figure 6:
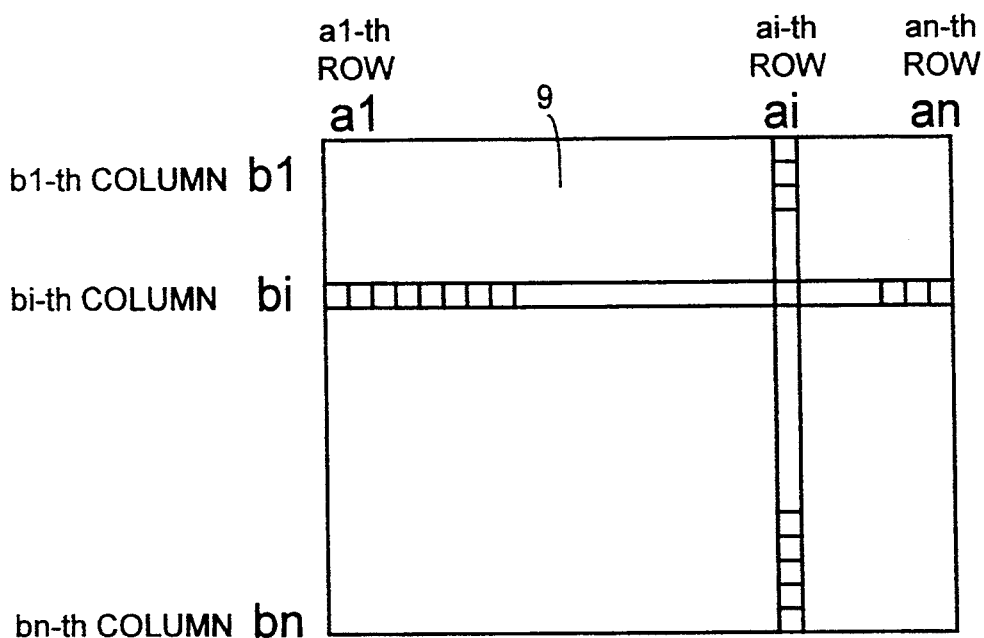
FIG. 6 is a view to explain the image in the case where frequency analysis is performed on the pixels which constitute the image.
Figure 7:
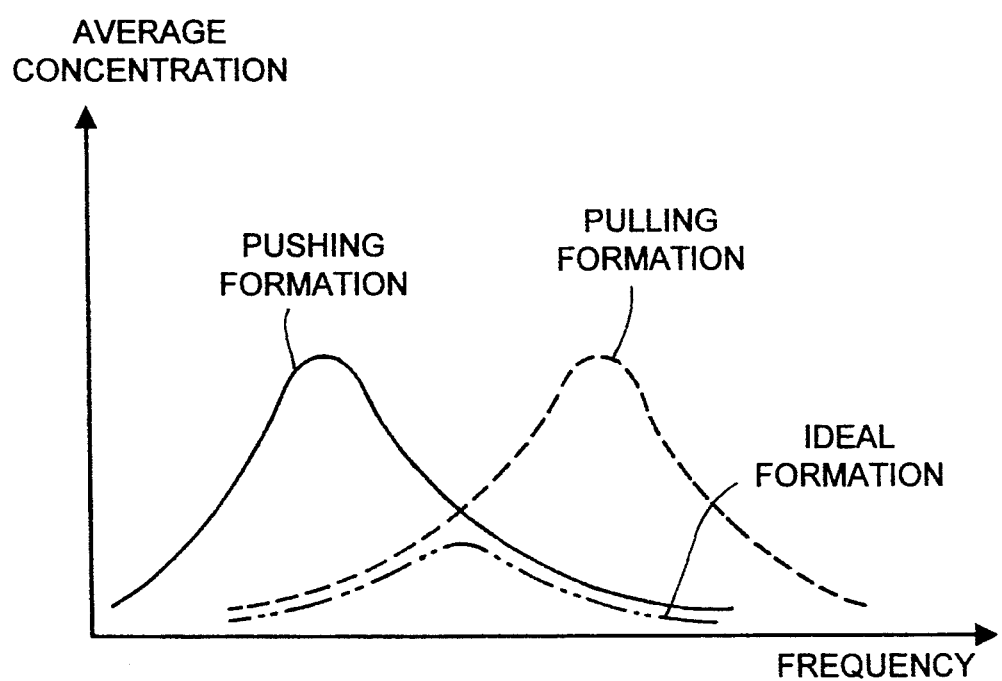
FIG. 7 is a diagram showing results of frequency analysis.

Connected to the image processing computing element 5 are a datum logger (not shown) for accumulating density datum for pixels of columns $a_1 - a_n$ in $b_i$-th row or rows $b_1 - b_n$ in $a_i$-th column composing the image 9 displayed on the display unit 6 as shown in FIG. 6 as well as an analyzer (not shown) for pulling out datum from the data logger to grasp them as changes over time for frequency analysis. Alternatively, the data accumulated in the data logger is processed by analysis software. Thus, judgment may be made whether the pulsating component is present or not in the paper 1 according to results of frequency analysis in longitudinal direction (along length of the paper 1). Frequency analysis in lateral direction (along width of the paper 1) may be made using stroboscope as the light source 2 unlike conventional way of transmitted light being caught by spot, so that features corresponding to the flock can be expressed, reproducing the density of formation with high fidelity. Accordingly, whether the formation is pulling formation or pushing formation can be easily judged. Pulling formation is the status where flock is extended in form of lines while pushing formation is the status where flock is in form of scales. In FIG. 7 with average density taken on ordinate and frequency on abscissa, the ideal formation is shown by two-dot chain line while pulling formation is given by solid line and pushing formation by broken line respectively.

Figure 8:
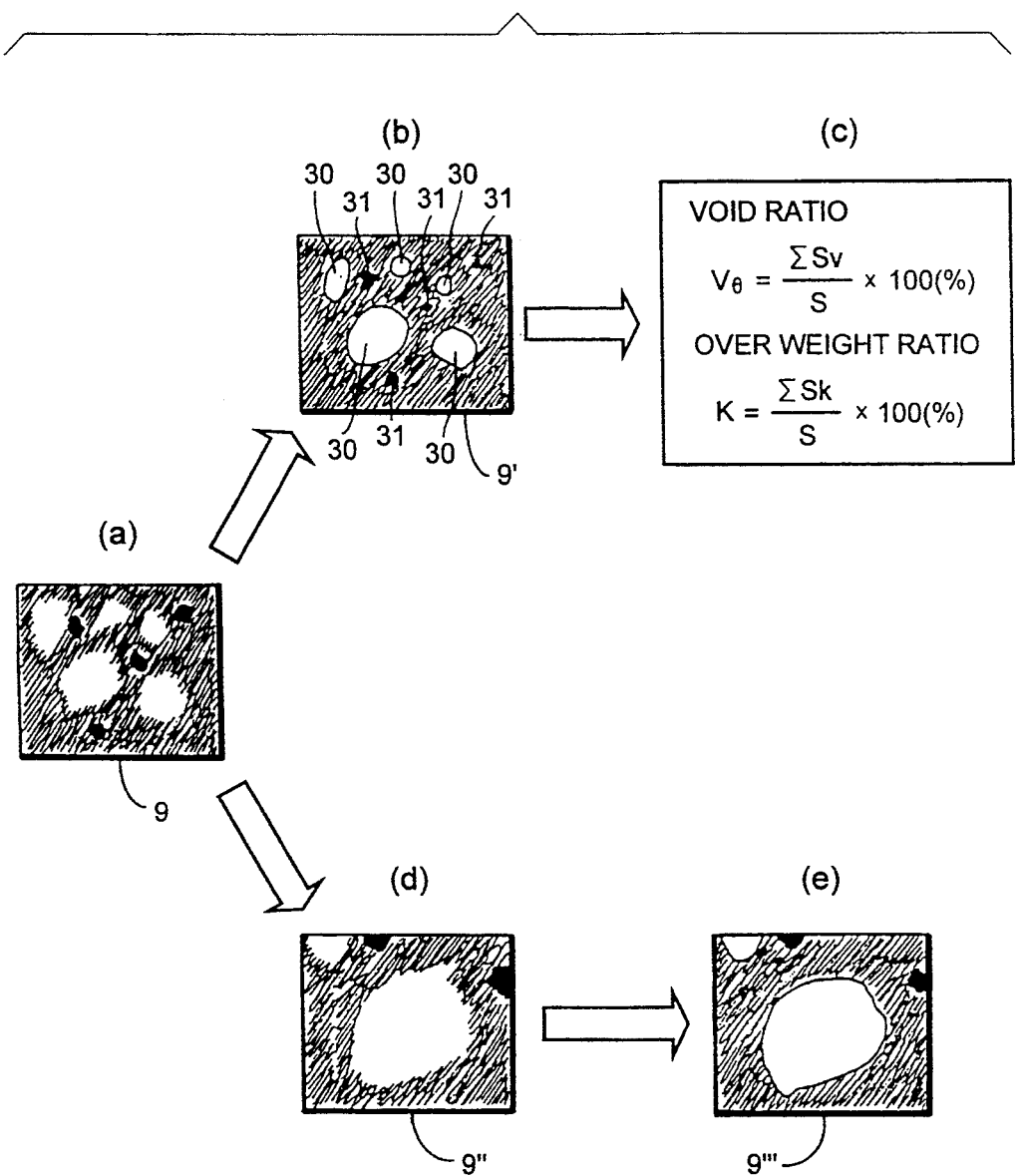
FIG. 8 is to explain a variation of image processing on image display in the formation measuring method of the present invention.

FIGS. 8($a$)–8($e$) show the variations in display of the image in the formation measuring method of the present invention. For more clarification of the image 9 displayed on the display unit 6, three-value image processing is performed, expressing the density by three steps of 'dense', 'moderate' and 'light' to display the image 9' as shown in FIG. 8($b$). The ratio of the sum $\Sigma S_V$ of areas 30 with maximum transmitted light on said image 9' to the total area S, i.e. void ratio $V_\theta$ is calculated as:

$$V_\theta = \frac{\Sigma S_V}{S} \times 100 \, (\%)$$

The ratio of the sum $\Sigma S_K$ of areas 31 with minimum transmitted light on said image 9' to the total area S, i.e. overweight ratio K is calculated as:

$$K = \frac{\Sigma S_K}{S} \times 100 \, (\%)$$

and displayed (FIG. 8 ($c$)). Thus, the formation of the paper 1 is quantitatively determined. If necessary, apparent defects in said image 9 or apparently satisfactory portions of the image 9 are displayed as enlarged image 9'' as shown in FIG. 8($d$) which is image-processed with expression of the density in three steps so that enlarged image 9''' of FIG. 8($e$) is displayed, which in turns is used as material for identification of the cause of the formation.

In the example shown in FIGS. 8($a$)–8($e$), plane information can be obtained by image processing with features of the paper 1 emphasized. Above all, holes, dust and the like which are not assessable in the past can be detected in earlier stage, thus contributing to improvement of quality and enhancement of productivity. Also, most satisfactory part or most unsatisfactory part of the image can be picked up and easily analyzed.

Figure 9:
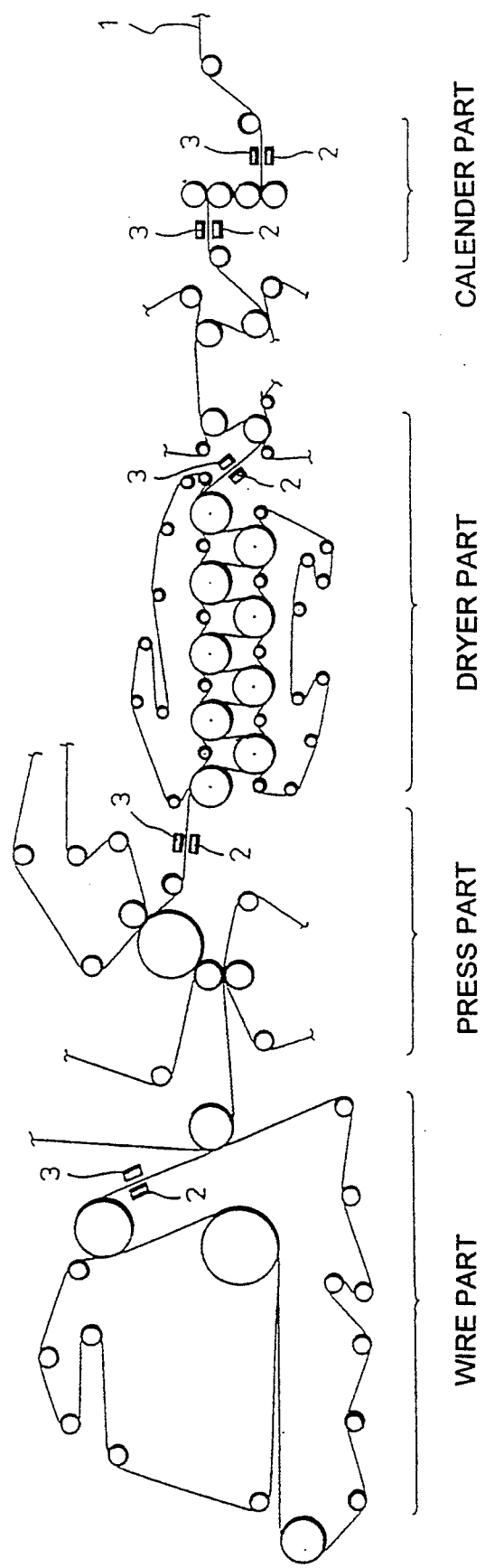
FIG. 9 is a general side view showing sites of installation of formation meters each comprising stroboscope and camera.

The formation meter comprising the light source 2 and the camera 3 used in the formation measuring method as described above may be installed in any cite such as wire part, press part, dryer part, calender part and like in FIG. 9.

Now, to determine the aperture of the camera 3 will be described.

Figure 10:
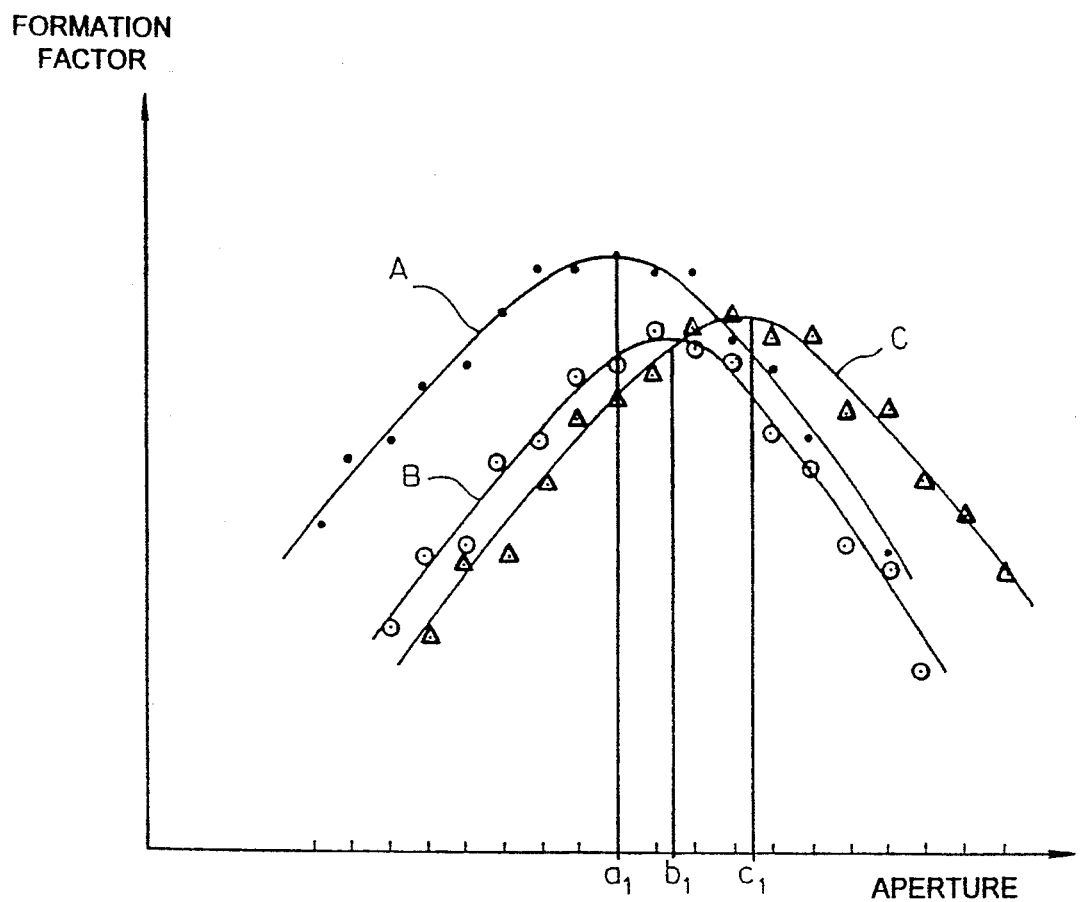
FIG. 10 is a variation curve diagram showing the relationship between camera aperture and formation factor.

One of the formation factors obtained above such as the average value $a_V$ of primary variance of density, secondary variance $V_{aV}$ of density, variance $V_{aaV}$ of average value of density, analytical specification of frequency in lateral direction and hole specification is named A, other as B, and still other as C, .... Values of formation factors A, B, C, ... are obtained with the aperture of the camera 3 being changed at constant interval as shown in FIG. 10. Results are variation curves having maximum or minimum values (maximum shown in the figure). Each maximum point $a_1, b_1, c_1, \ldots$ of the curves most typically represents the features of the formation factors A, B, C, ..., respectively.

Figure 11:
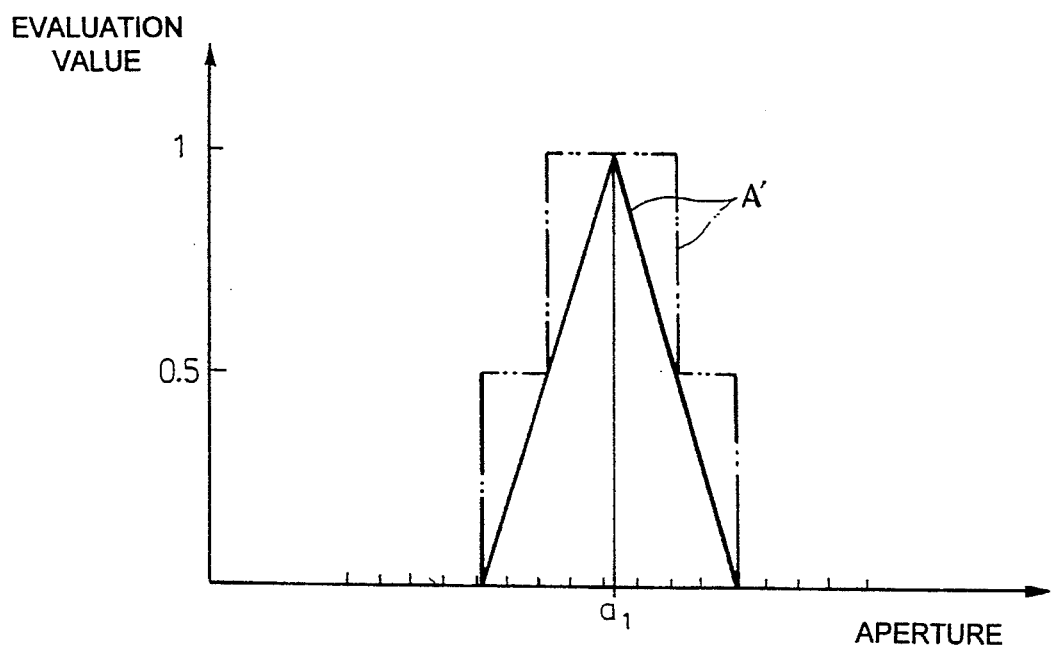
FIG. 11 is a diagram showing a membership function obtained on one of the formation factors.
Figure 12:
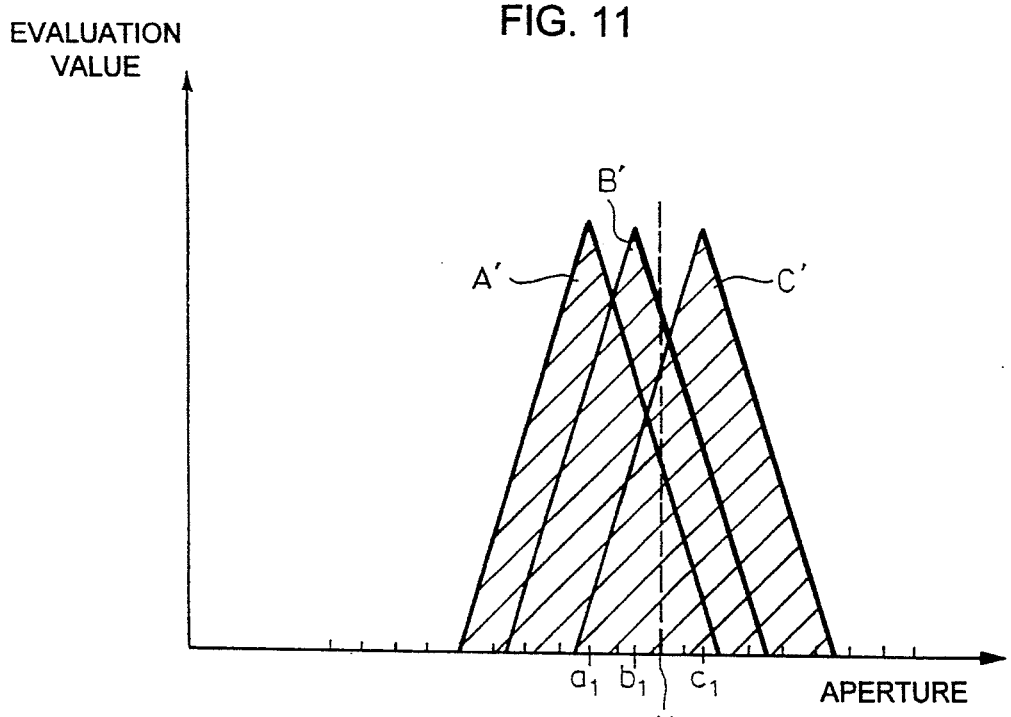
FIG. 12 is a diagram showing how to obtain the center of gravity by synthesizing the membership functions to the variation curves of a plurality of formation factors.

Through the data processing of each of the variation curves of the formation factors A, B, C, ..., membership functions in triangular or rod-like form as shown in FIG. 11 (only the membership function A' related to formation factor A is given in the figure) is obtained with evaluation value of maximum being 1. By synthesizing each of the membership functions A', B', C', ... thus obtained, a center of gravity X (center of gravity of the area) is obtained as given in FIG. 12.

This point X is the aperture of the camera 3.

The aperture of the camera 3 is automatically adjusted by the control signal from the image processing computing element 5 to the automatic aperture device 3$b$ so that the aperture will be equal to the value thus obtained.

By the above procedure, the aperture of the camera 3 can be automatically selected so that the most characteristic information of the sample can be obtained. Accordingly, formation can be measured more accurately, causing no individual difference in measurement results.

Thus, it is possible to quantitatively determine the formation as plane, not as points like the prior art, and to evaluate formation more accurately and objectively, and further to utilize the formation factors for the control of J/W ratio, drainage and the like.

Use of stroboscope as the light source 2 will make it possible to apply the formation measuring method as described above not only to off-line operation but also to on-line operation with high speed (1500 m/min. or so) and high basis weight (basis weight: about 300 g/m²).

Advantages in the use of stroboscope as light source 2 are as follows:

(1) There is less deviation of screen during high-speed on-line measurement and no trouble occurs on the analysis of pixels on the screen due to the deviation on screen.

(2) When shuttering the camera, density can be expressed in three steps of 'dense', 'moderate' and 'light' to clearly define the image up to the analysis of three-value imaging; but it is not suitable for detecting slight density such as formation meter. Combination of stroboscope with non-shuttering camera is more suitable for high-speed photographing to detect the density.

(3) Because high light quantity can be easily obtained by stroboscope (pulse light source), (a) the aperture of camera can be reduced during photographing, which minimizes the influence of disturbance, and (b) even thicker paper can easily transmit light.

(4) There is speed limit in using mechanical shuttering whereas, needless to say, combination of stroboscope with electrical shuttering enables photographing of image at higher speed.

Advantages of CCD frame accumulated mode camera are that still image can be photographed by stroboscope and the image signal can be equally incorporated.

Next, description is given on the method for controlling formation through application of the concept of membership function based on the formation factors obtained by the above formation measuring method (See R. Yamakawa: 'Concept of Fuzzy Computer'; Nov. 10, 1988, 3rd print; Kodansha).

The control is performed through fuzzy control unit 110 comprising the control computer 100 and the controller 101 in FIG. 3 based on the formation factors obtained by the image processing computing element 5.

Figure 13:
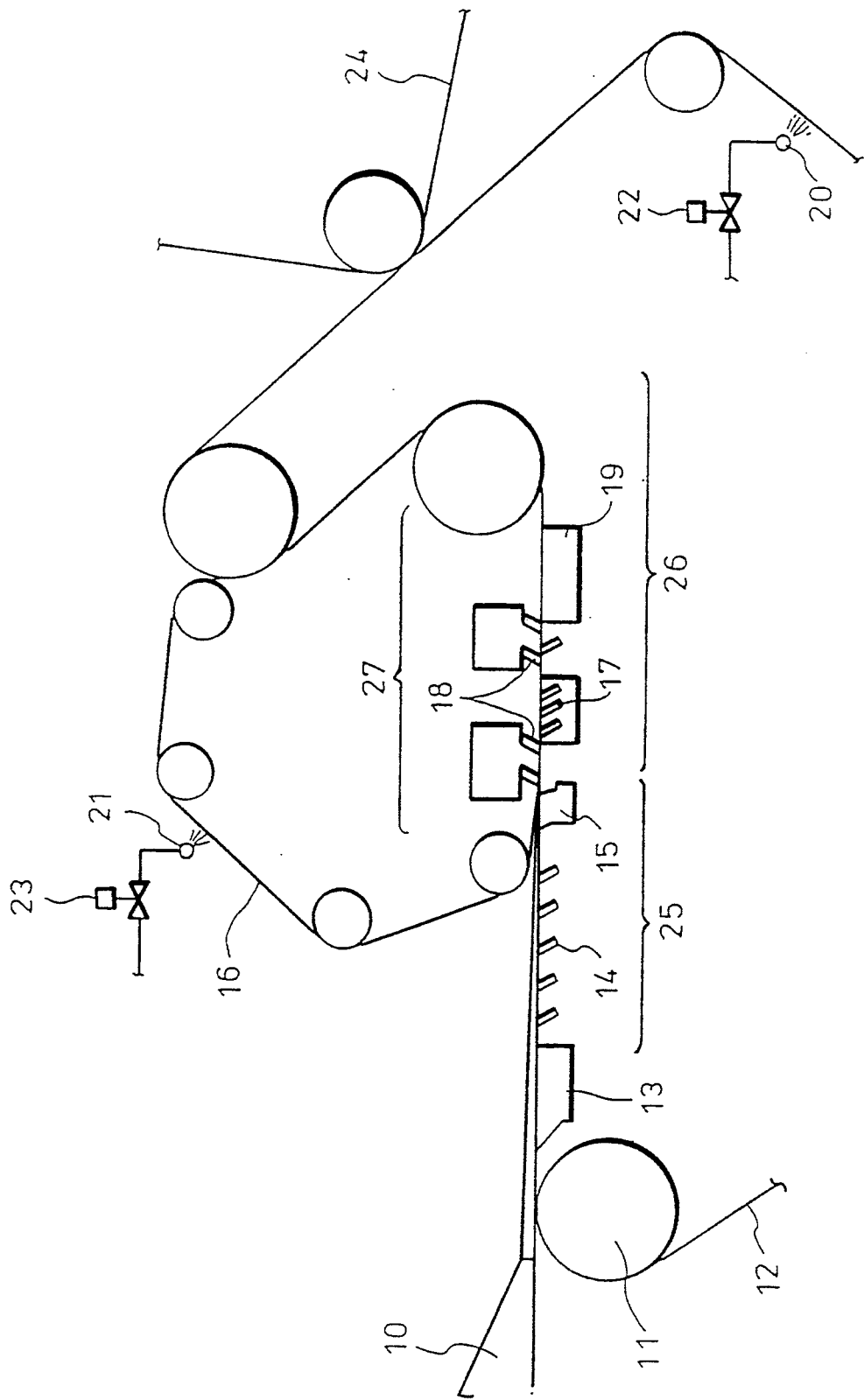
FIG. 13 is a side view of wire part of a paper machine.

FIG. 13 is a side view showing the wire part of a paper machine, where 10 represents a head box; 11, a breast roll; 12, bottom wire; 13, a forming board; 14, foils; 15, a wet suction box; 16, top wire; 17 and 18, deflectors; 19, a suction box; 20 and 21, showers to wash off dust attached on bottom wire 12 and top wire 16; 22 and 23, automatic valves for adjusting quantity of water from the showers 20 and 21; and 24, felt. The foils 14 are drainage elements of the initial drainage area 25. The angle of the foils 14 with respect to the bottom wire 12 may be adjusted to alter the pressure applied by suction from the drainage area. Deflectors 17,18 form part of the secondary drainage area 26, 27. There is an overlap along the bottom wire 12 between the top edge of the bottom deflector 17 and the bottom edge of the top deflector 18. The relative clearance between the top and bottom edges is known as the deflector pushing degree. The deflector pushing degree and angles of the deflectors are both adjustable to affect the secondary drainage parameters. J/W ratio (the ratio of jet speed injected from the head box 10 to the speed of bottom and top wires 12 and 16), angles of the foils 14 at an initial drainage area 25, pushing degrees of the deflectors 17 and 18 at a bottom secondary drainage area 26 and at a top secondary drainage area 27 are changed respectively according to the formation factors obtained by the above formation measuring method. Suction quantity of the suction box 19 and openings of the automatic valves 22 and 23 of the showers 20 and 21 are changed if necessary.

The method of the invention wherein generated membership curves are used in conjunction with operation factors of a paper making apparatus to optimize to paper quality will now be explained with reference to FIG. 14, as set forth in steps (1) through (4) below. Based on experimental data performed in advance, membership function curves are obtained in advance as shown in FIGS. 14($i$)–14($v$): (1) five membership functions curves for formation $M_1$–$M_5$ to specify the quality of the paper 1 in five steps of 'worst', 'bad', 'normal', 'good' and 'best' from the degree (ordinate) corresponding to formation factor (abscissa) of the paper 1 and (2) five membership function curves for control $M_{1a}$–$M_{5a}$ and $M_{1b}$–$M_{5b}$ to the corresponding degree (ordinate) to the changes (abscissa) of J/W ratio (only increase or decrease of wire speed in this case) in response to each of the membership function curves $M_1$–$M_5$ to specify the quality of the paper 1.

(3) Degree of matching at intersections of the formation factors of the paper 1 obtained by the formation measuring method with each of the membership function curves $M_1$–$M_5$ to specify the quality of the paper 1 is obtained. (4) In correspondence to each of the matching degrees, results of the estimated J/W ratio changes are obtained from the respective membership function curves $M_{1a}$–$M_{5a}$ and $M_{1b}$–$M_{5b}$ showing changes of the J/W ratio. Further, results of the estimated change of J/W ratio are overlapped and synthesized and final membership functions $M_{La}$ and $M_{Lb}$ showing final estimated results of the J/W ratio change are found as shown in FIG. 14($vi$). Abscissa component of either of the gravity centers of the final membership functions $M_{La}$ and $M_{Lb}$ where the area surrounded by final membership function $M_{La}$ ordinate or $M_{Lb}$ ordinate and abscissa is halved is used as increment or decrement of the actual wire speed, determining actual change of J/W ratio for control of J/W ratio.

FIG. 14 shows a case where the formation factor is 35. Since ordinate component (matching degree) of the intersection with the membership function curve $M_1$ showing 'worst' of FIG. 14($i$) is about 0.25, the head of the control membership function curve $M_{1a}$ or $M_{1b}$ to 'extensively increase' or 'extensively decrease' wire speed by extending the line horizontally from the intersection is scraped off at about 0.25 of the matching degree and only hatched portion is adopted as estimated result of increment or decrement of the wire speed. Also, since ordinate component (matching degree) of the intersection with the membership function curve $M_2$ showing 'bad' of FIG. 14($ii$) is about 0.75, the line from the intersection is extended, the head of the control membership function curve $M_{2a}$ or $M_{2b}$ to 'increase' or 'decrease' wire speed is scraped off at about 0.75 of matching degree and only hatched portion is adopted as estimated result of increment or decrement of the wire speed. Further, since ordinate component (matching degree) of the intersection with the membership function $M_3$ showing 'normal' of FIG. 14(iii) is about 0.7, the line from the intersection is extended horizontally, the head of control membership function curve $M_{3a}$ or $M_{3b}$ to 'fairly increase' or 'fairly decrease' the wire speed is scraped off at about 0.7 of the matching degree and only hatched portion is adopted as estimated results of increment or the decrement of wire speed. Also, since ordinate component (matching degree) of the intersection with the membership function curve $M_4$ showing 'good' of FIG. 14(iv) is about 0.1, the line from the intersection is extended horizontally, the head of the control membership function curve $M_{4a}$ or $M_{4b}$ to 'slightly increase' or 'slightly decrease' the wire speed is scraped off at about 0.1 of the matching degree and only hatched portion is adopted as estimated result of increment or decrement of the wire speed. Further, with the formation factor being 35 in relation to the membership function curve $M_5$ showing 'best' of FIG. 14(v), there is no intersection. Therefore, the matching degree to the control membership function curve $M_{5a}$ or $M_{5b}$ to 'not increase' or 'not decrease' the wire speed is 0, i.e. it is necessary to increase or decrease the wire speed. Accordingly, with the formation factor being 35 or so, overlap and synthesis of the estimated results lead to the center of gravity being located between 'fairly increase' and 'increase' or between 'fairly decrease' and 'decrease' where matching degree is relatively high as shown in FIG. 14(vi) and increment or decrement of wire speed is determined. For the judgment on whether to increase or to decrease the wire speed, one of the centers of gravity (e.g. the center of gravity to decrease) is adopted from the final estimated result. In the case where improvement of formation is noted (i.e. the difference between the formation factor before the control and the formation factor during the control is positive), control is performed to decrease the wire speed. In the case where improvement of formation is not noted (i.e. the difference between formation factor before the control and the formation factor during control is negative), control is performed thereafter in the direction to increase the wire speed. Thus, more efficient control can be achieved.

In this way, by adopting the fuzzy theory using membership functions, it is possible to perform not on-off control but mild control without giving radical change on the paper 1.

Figure 15:
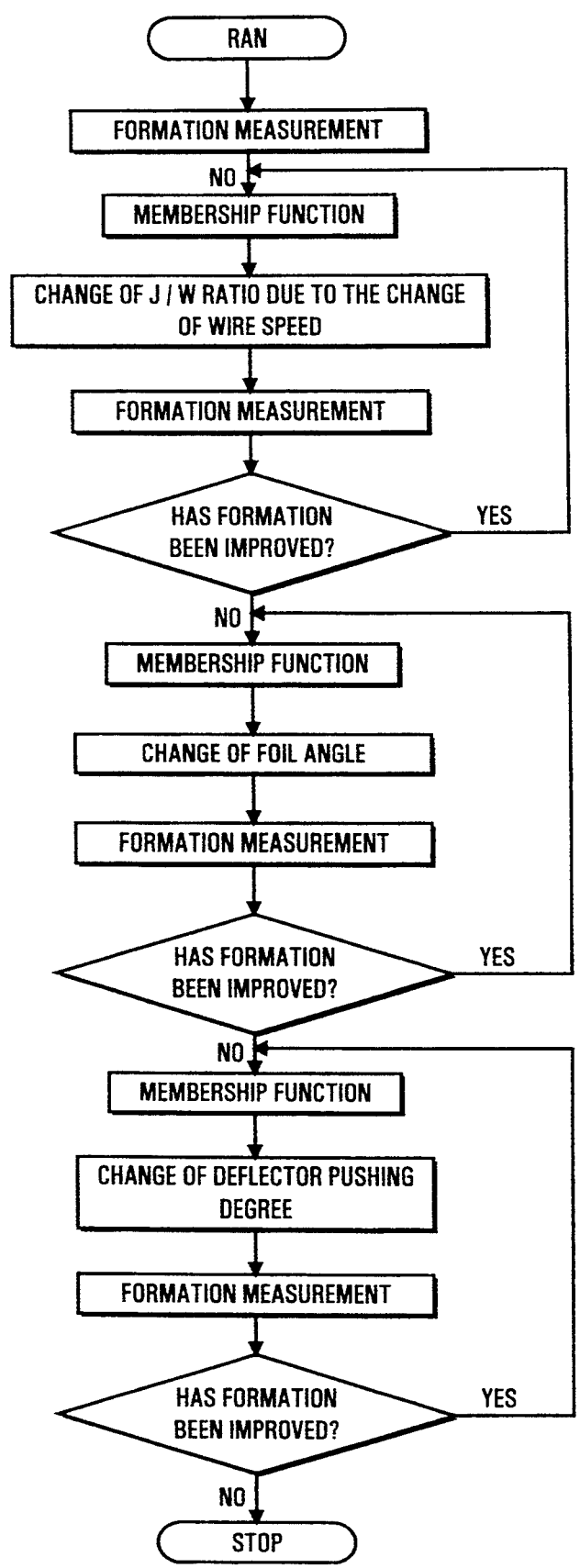
FIG. 15 is a flow chart of an example of the formation controlling method using the formation measuring method of the present invention.

When J/W ratio is changed in this way and no further improvement of formation is found by the repeated change of J/W ratio as shown in FIG. 15, the formation is improved by a fine tuning method by controlling in sequence the foil angle until no further improvement is noted, and then the deflector pushing degree until no further improvement is noted.

In controlling the J/W ratio, it is possible to increase J/W ratio in the case of pulling formation and to decrease J/W ratio in the case of pushing formation, using the results of frequency analysis (i.e. whether the formation is pulling or pushing) of the density of the image in lateral direction. In so doing, formation control can be achieved reliably and efficiently.

Further, it is possible to observe the entire formation by lifting the camera 3 along the rail 3c in FIG. 3 to widen visual field of the camera 3 at the starting of measurement. The visual field of the camera 2 is gradually narrowed down by moving down the camera 3 along the rail 3c as the formation is improved by the formation control method after starting the control. When the formation is substantially stabilized and the control is almost completed, the camera 3 may be lifted up again along the rail 3c to return to the initial large visual field for monitoring.

This contributes to the fine control of the formation and is useful to cope with changes of external conditions such as change of raw material condition after the formation is stabilized.

Figure 16:
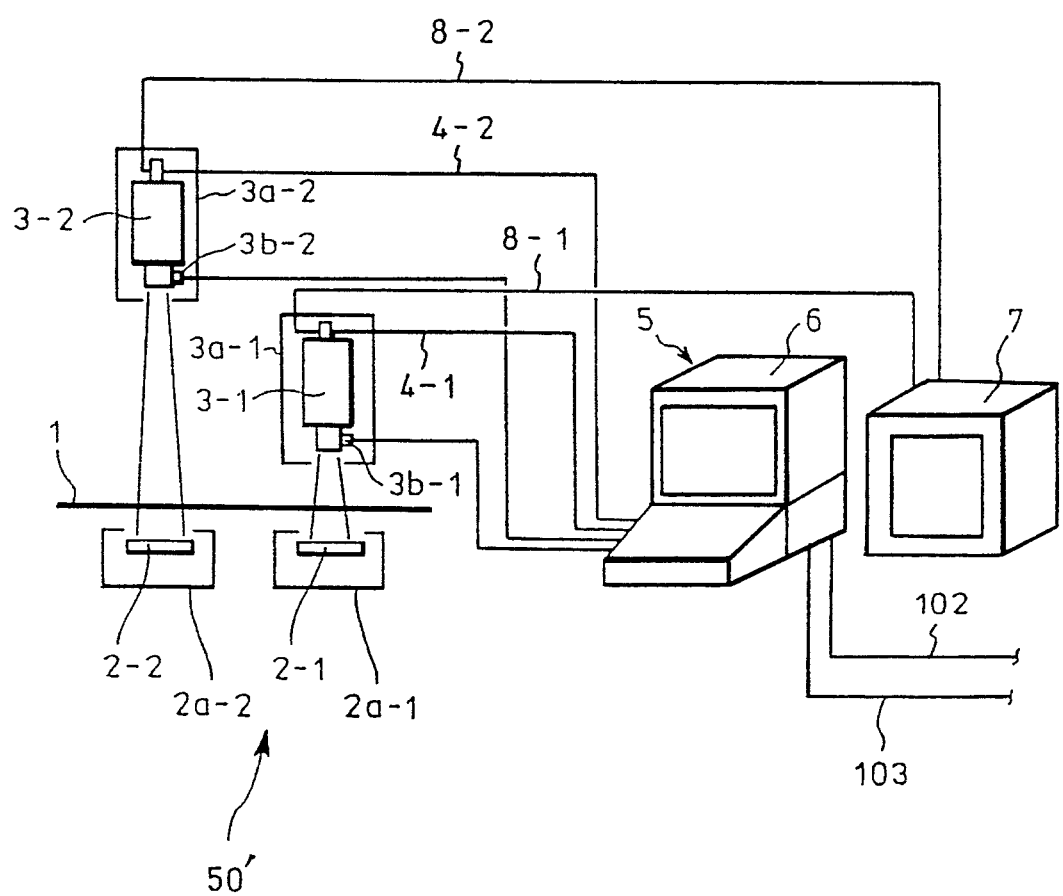
FIG. 16 shows an arrangement of another embodiment comprising a plurality of cameras with different visual fields.

FIG. 16 shows another embodiment of the changed visual field in which automatic aperture devices 3b-1 and 3b-2 are incorporated. A plurality of (two in the figure shown) cameras 3-1 and 3-2 accommodated in camera boxes 3a-1 and 3a-2 are arranged on one side of the paper 1, and the light sources 2-1 and 2-2 accommodated in light source boxes 2a-1 and 2a-2 are arranged on the other side to make up a formation meter 50'. It is preferable to dispose the cameras 3-1 and 3-2 in the feeding direction of the paper 1.

Before starting and after completion of the control, the image is caught by the camera 3-2 with wider visual field and its signal is sent through the cable 8-2 to the display unit 7 and through the cable 4-2 to the image processing computing element 5. When the formation is improved after the starting of control and requirements for judging fine variance can be met, changeover to the camera 3-1 with narrower visual field is effected. Its signal is sent to the display unit 7 through the cable 8-1 and to the image processing computing element 5 through the cable 4-1 for further processing.

Although a plurality of cameras are required for such procedure, the cameras need not to be moved for change of visual field and may be fixed. The visual field can be quickly changed simply by switching over the plural cameras.

Figure 17:
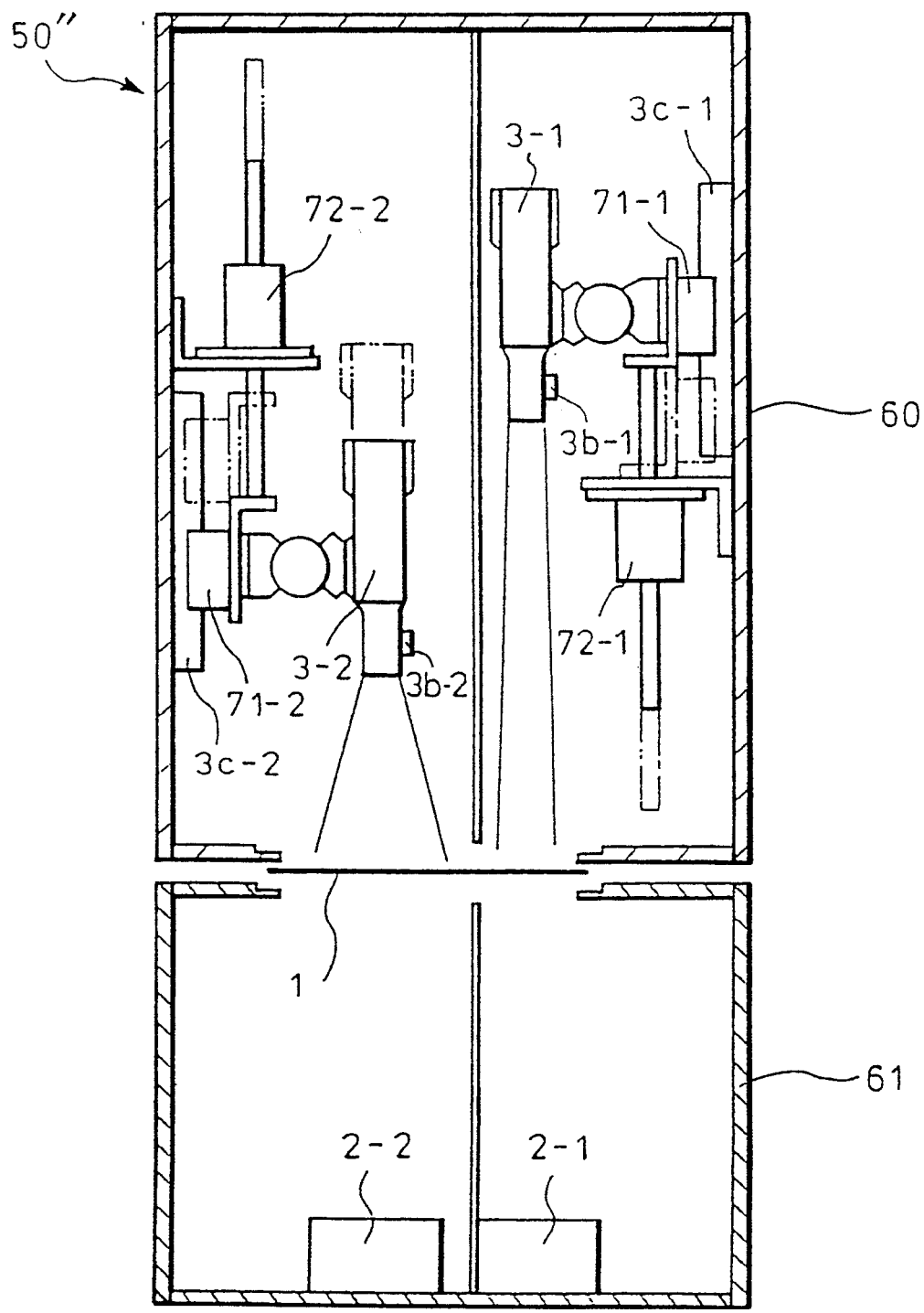
FIG. 17 is a lateral sectional view of a formation meter which grasps or catches images in wide and narrow visual fields.
Figures 18A, 18B:
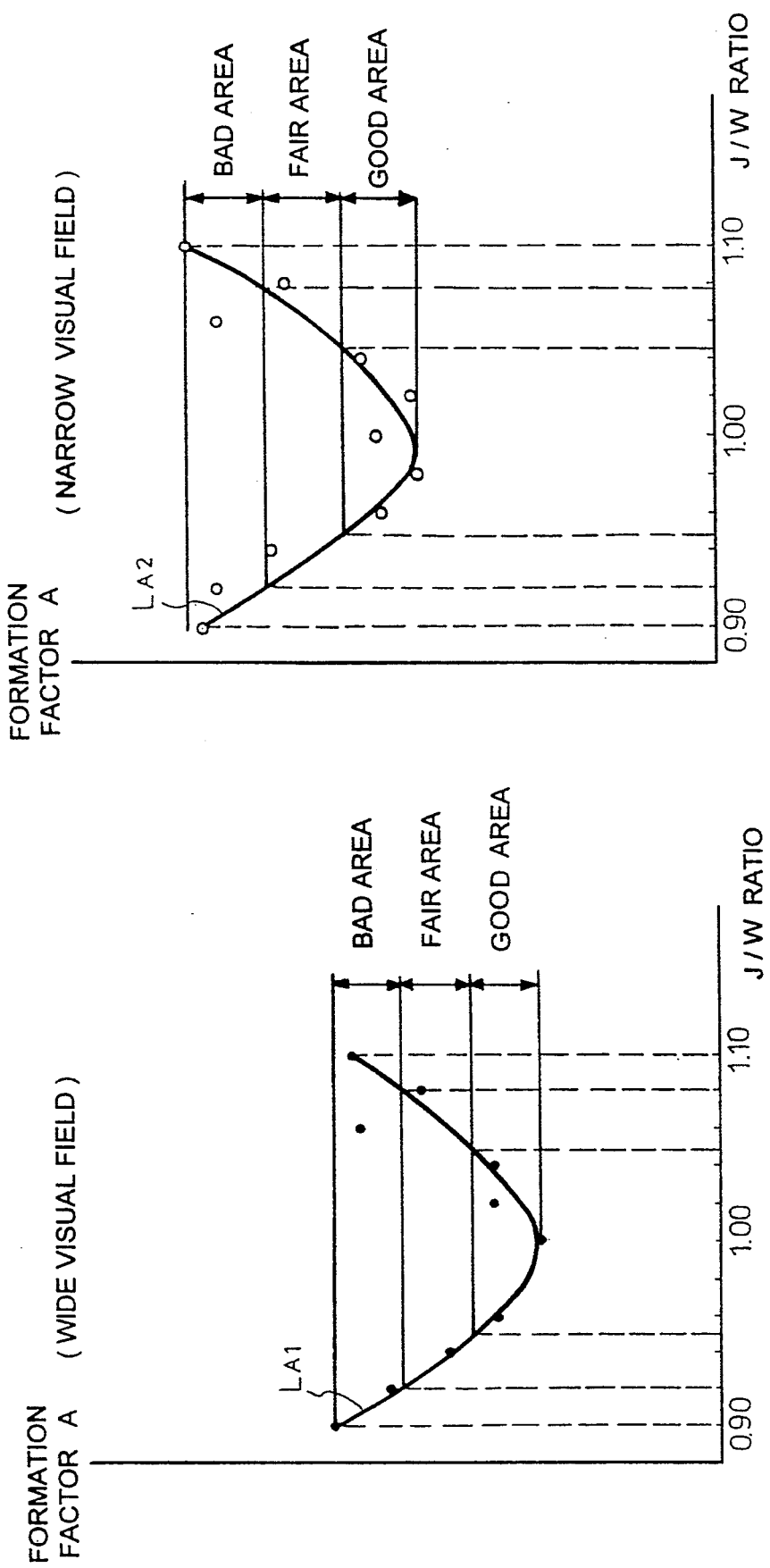
FIGS. 18(a) and 18(b) are variation curve diagrams showing the relationship between J/W ratio and formation factor A.
Figure 19A:
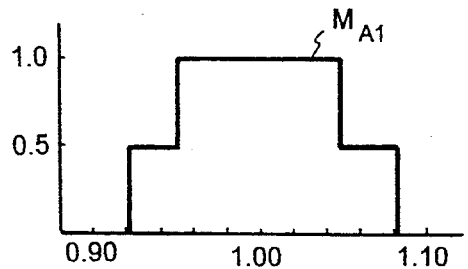
FIGS. 19(a) and 19(b) are membership function diagrams showing the relationship between J/W ratio and evaluation values for formation factor A.
Figure 22A:
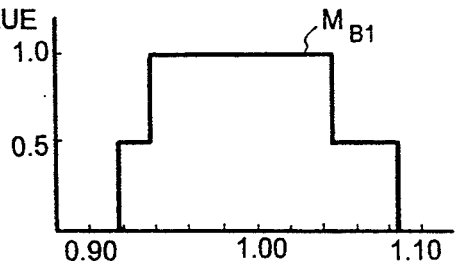
FIGS. 22(a) and 22(b) are membership function diagrams showing the relationship between J/W ratio and evaluation values for formation factor B.
Figure 19B:
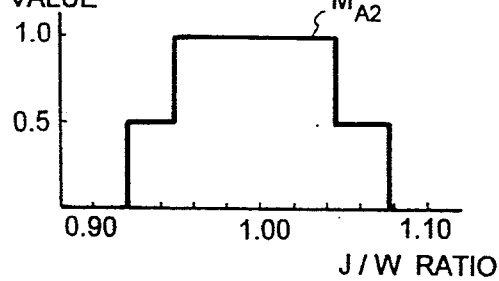
Figure 22B:
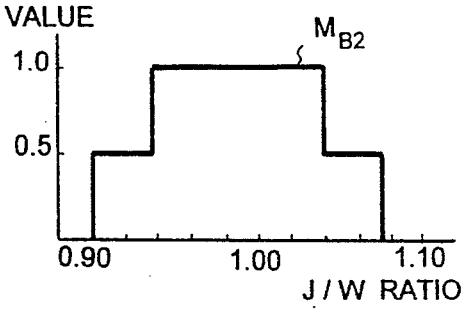

FIG. 17 shows a formation meter 50" in which images in wide and narrow visual fields are concurrently caught by a plurality of cameras with different visual fields and each of these images are introduced to the image processing computing element 5 (FIG. 3). In this formation member 50", support stands 71-1 and 71-2 are installed vertically movably along the rails 3c-1 and 3c-2 fixed in a upper main body frame 60 by drives 72-1 and 72-2 such as linear motors. The support stands 71-1 and 71-2 have thereon cameras 3-1 and 3-2 such as CCD (charge coupled device) frame accumulation mode cameras having automatic focusing function as well as automatic aperture devices 3b-1 and 3b-2. Further, light sources 2-1 and 2-2 such as parallel light sources with variable light quantity or stroboscopes are placed in a lower main body frame 61 opposedly to the above cameras 3-1 and 3-2.

When measurement is performed on on-line basis in the formation meter 50", the paper 1 on the line is fed between upper and lower main body frames 60 and 61 and images by transmitted lights from the light sources 2-1 and 2—2 and coming through the paper 1 are caught by the cameras 3-1 and 3-2. On the other hand, in the case where measurement is performed on off-line basis, the paper 1 as sample is set between the upper and lower main body frames 60 and 61 and images by the transmitted light from the light sources 2-1 and 2—2 and coming through the paper 1 are caught by the cameras 3-1 and 3-2. The image from the light source 2—2 caught by the camera 3-2 is in wide visual field while the image from the light source 2-1 caught by the camera 3-1 is in narrow visual field. Connected to the formation meter 50" shown in FIG. 17 are the image processing computing element 5 and the fuzzy control unit 110 similar to those in FIG. 3, though not shown in the figure.

FIGS. 18 to 24 show a procedure to control the formation by obtaining optimal value of J/W ratio, using the formation meter 50″ shown in FIG. 17. Description is now given in detail on this procedure. Range of the J/W ratio change is set to a predetermined range (e.g. 0.90 –1.10) and the range of the change is equally divided (e.g. into 10 equal parts). For the paper 1 with J/W ratio being set to a predetermined value (e.g. 0.90), images are caught by the lights from the light sources 2—2 and 2-1 passing through the paper 1 by the cameras 3-2 and 3-1 in wide and narrow visual fields, respectively. Based on each image, the formation factors A and B are obtained by the image processing computing element 5 from average primary variance $a_V$ of density, secondary variance of density $V_{aV}$, variance $V_{aaV}$ of the average value of density, frequency analysis specification in lateral direction and hole specification. By the same procedure, the formation factors A and B are sequentially obtained for the paper 1 in the case where the range of the J/W ratio change is equally divided. As shown in FIGS. 18(a), 18(b), 21(a) and 21(b), variation curves $L_{A1}$, $L_{A2}$, $L_{B1}$ and $L_{B2}$ showing the relationship between J/W ratio and the formation factors A and B in wide and narrow visual fields are obtained. The formation factors are not limited to A or B and variation curves may be obtained further for formation factors C, D. . . .

Then, by the fuzzy control unit 110, in each of the above variation curves $L_{A1}$, $L_{A2}$, $L_{B1}$ and $L_{B2}$, the area from lower to upper limit of the formation factors A and B is for example equally divided into three parts in the direction of ordinate to 'good area', 'fair area' and 'bad area'. Evaluation values for these good, fair and bad areas are set to 1.0, 0.5 and 0.0 as shown in FIGS. 19(a), 19(b), 22(a) and 22(b) to obtain membership functions $M_{A1}$, $M_{A2}$, $M_{B1}$ and $M_{B2}$ showing the relationship between J/W ratio and evaluation values in wide and narrow visual fields.

Figure 20:
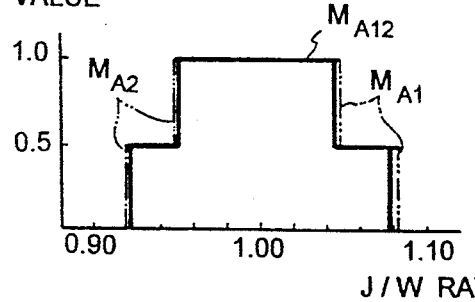
FIG. 20 is a wide-narrow visual field membership function diagram obtained by overlapping FIGS. 19(a) and 19(b)
Figure 23:
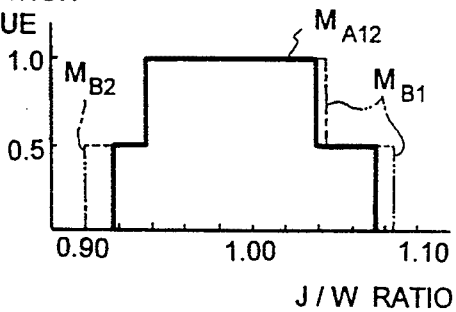
FIG. 23 is a wide-narrow visual field membership function diagram obtained by overlapping FIGS. 22(a) and 22(b)
Figure 24:
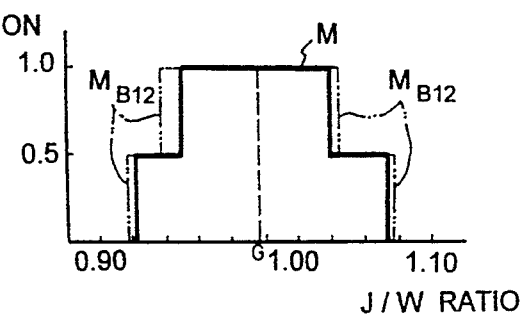
FIG. 24 is a general membership function diagram obtained by overlapping FIGS. 20 and 23.
Figure 21B:
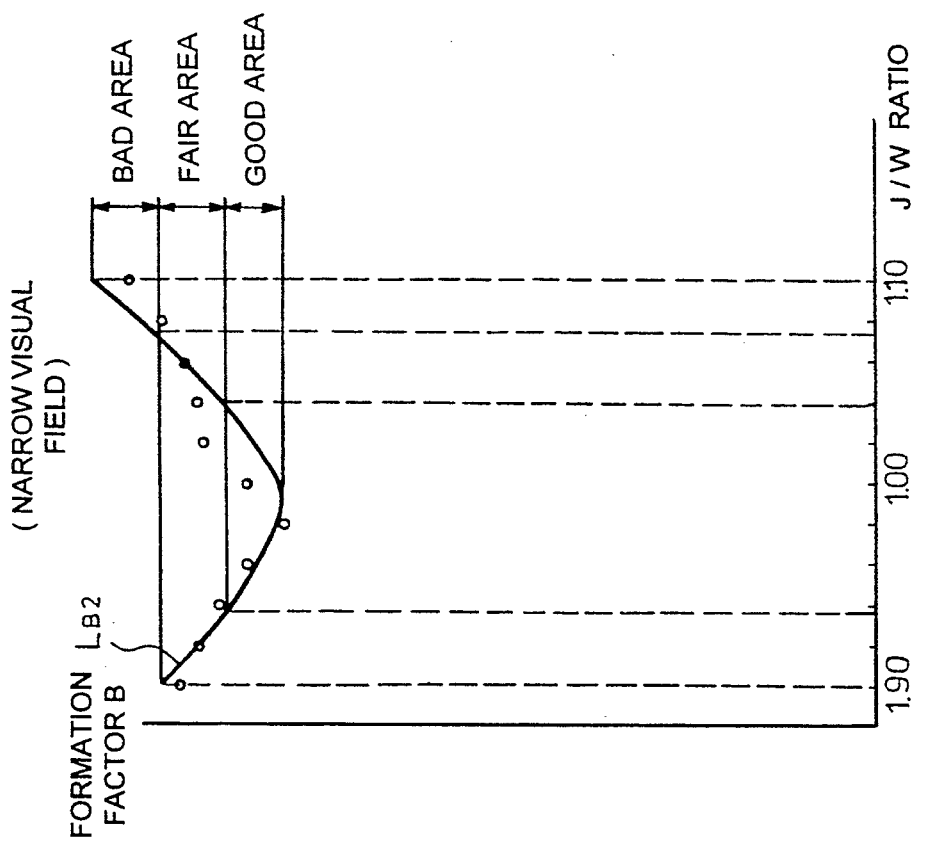
FIGS. 21(a) and 21(b) are variation curve diagrams showing the relationship between J/W ratio and formation factor B.
Figure 21A:
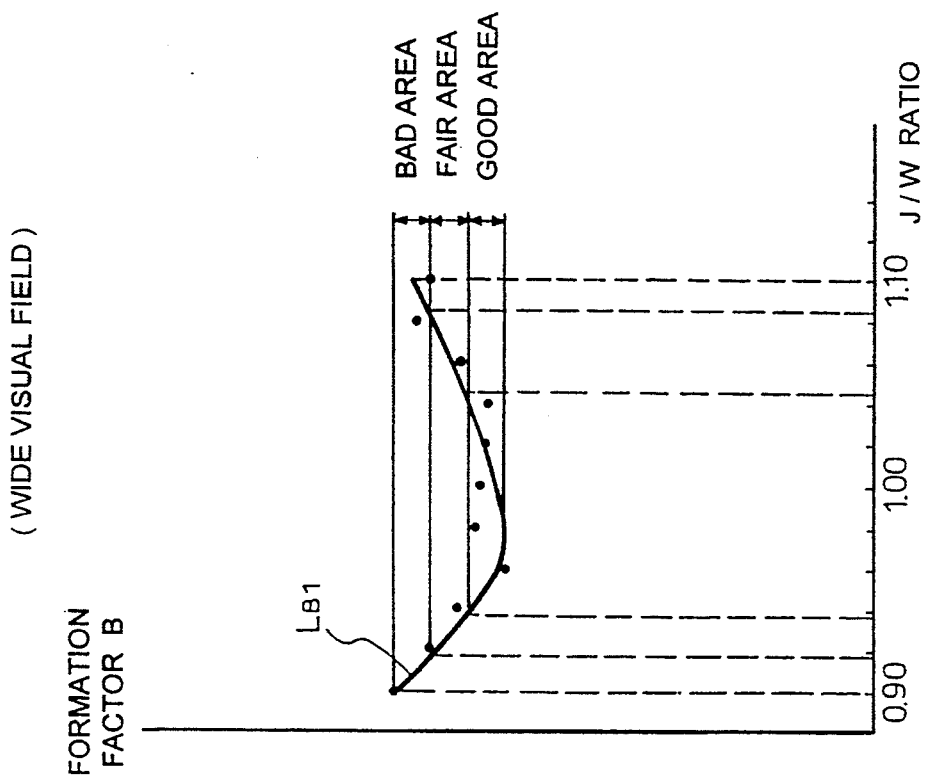

Next, the membership functions $M_{A1}$ and $M_{A2}$ are overlapped to obtain wide-narrow visual field membership function $M_{A12}$ as shown in FIG. 20 for the formation factor A through adoption of only a portion where the above two functions overlap each other. The membership functions $M_{B1}$ and $M_{B2}$ are overlapped to obtain wide-narrow visual field membership function $M_{B12}$ as shown in FIG. 23 for the formation factor B through adoption of only a portion where two functions overlap each other. Further, the above wide-narrow visual field membership functions $M_{A12}$ and $M_{B12}$ are overlapped with each other to obtain overall membership function M as shown in FIG. 24 through adoption of only a portion where two functions overlap on each other. The center G of gravity of the area surrounded by this overall membership function M is obtained and is selected as optimal J/W ratio. J/W ratio is controlled to become the optimal J/W ratio. Alternatively, the membership functions $M_{A1}$ and $M_{B1}$ may be overlapped with each other.

By the same procedure, center of gravity is obtained from overall membership function for initial drainage by foils and the initial drainage control is performed so that foil angle takes optimal value. Also, for finishing drainage by deflector, center of gravity is obtained from overall membership function and the finishing drainage is controlled so that the deflector pushing degree and angle take optimal values.

Above all, in the case where there are two or more deflectors as drainage elements in the finishing drainage, membership functions are obtained by changing combination of pushing degree with angle and optimal values of pushing degree and angle are obtained for each deflector. Also, in the case where there are two or more foils in the initial drainage, membership functions are obtained by changing combination of angles of each foil and optimal value of angle is obtained for each foil.

Thus, membership functions are not prepared from the beginning in fuzzy control. But, control variables are respectively changed such as J/W ratio, foil angle in initial drainage, deflector pushing degree and angle in finishing drainage and evaluation values for each case are combined to generate an overall membership function. As the result, more reliable control can be achieved and production of various types of paper can be properly controlled.

Further, because the cameras 3-2 and 3-1 are arranged for different wide and narrow visual fields as sensors and the sample information is simultaneously obtained, formations can be obtained both macroscopically and microscopically as numerical values and control closer to control by human vision can be accomplished. As described above, fuzzy control is performed for J/W ratio, initial drainage and finishing drainage. Then, the range of the change around the optimal value of J/W ratio is set smaller than the range of the J/W ratio change in the previous fuzzy control and J/W ratio is sequentially changed within the smaller range of the change. By the same procedure as above, center of gravity is obtained from overall membership function and J/W ratio control is performed so that J/W ratio takes an optimal value obtained from the center of gravity this time. Initial and finishing drainages are also controlled such that the foil angle and deflector pushing degree take optimal values obtained from center of gravity this time.

Figure 25:
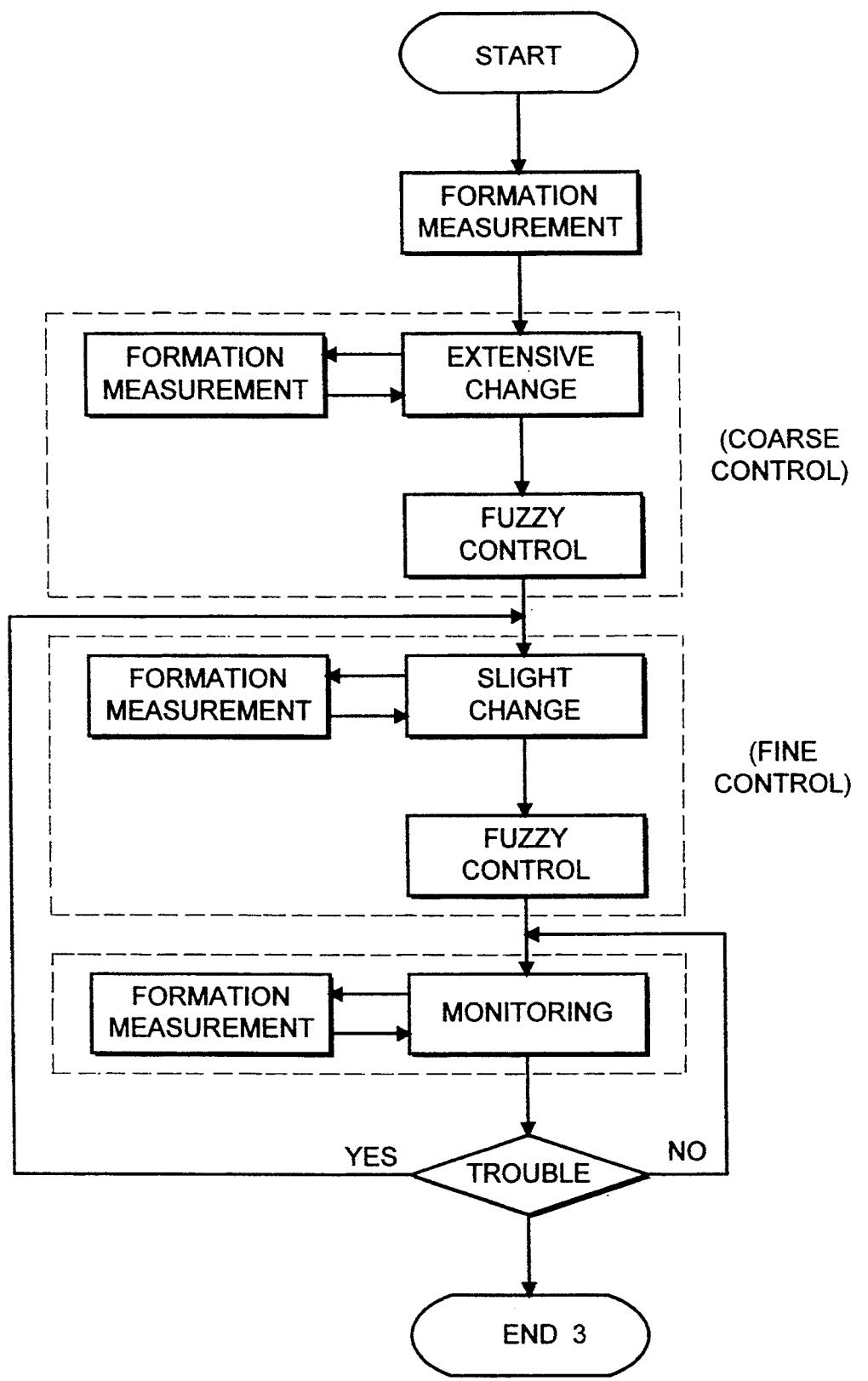
FIG. 25 is a flow chart showing the flow of coarse and fine controls.

Thereafter, watching is effected and continued unless any trouble occurs. When any trouble is detected such as decrease of formation due to external change including raw material conditions, control is restarted as described above (See FIG. 25).

In this way, range of the change of control variables such as J/W ratio, foil angle in the initial drainage and deflector pushing degree and angle in the finishing drainage, etc. are initially set to large values for coarse control. After coarse control is completed, range of the changes of each of the above control variables is set to smaller values and fine control is performed. Thus, in the initial stage of paper-making, products with considerable quality can be produced by the coarse control with satisfactory yield and products of high quality with good formation are obtained by the fine control.

Further, because the data obtained during fine control are accumulated, production of the same type of paper can be controlled later by only fine control. Reprocessing and rise-up times can be shortened and waste of products during reprocessing and rise-up operations can be eliminated.

What is claimed is:

1. A method for generating a paper quality membership function to be used in an apparatus for controlling the degree of fiber variance in paper sheet, comprising the steps of:
   (a) picking up an image of transmitted light from a light source on an area of paper by a plurality of cameras with different visual fields, the cameras being arranged so that images of the transmitted light are picked up by the cameras concurrently in comparatively wide and narrow visual fields and are introduced to a display unit of an image processing computing element, there being means provided for changing the visual field introduced to the display unit;

(b) dividing the image of the transmitted light on the display unit into a predetermined size and number of windows, the windows comprising pixels;

(c) measuring the tone density of each pixel, and the tone density of each window from the tone density of the pixels comprising the window;

(d) calculating values chosen from at least one of the following:
  an average value of tone density and a primary variance of tone density of each window from the tone density of each pixel,
  an average value of the primary variance of the tone density for all of the windows,
  a secondary variance of tone density for all of the windows, and
  a variance of average values of tone density of each window; and (e) using one of or at least two in combination of said values as a formation factor;

(f) changing the visual field transmitted to said display unit by said plurality of cameras;

(g) repeating steps (a)-(e) one or more times to obtain different formation factors;

(h) generating a paper quality membership function from the different formation factors obtained: and (i) using said paper quality membership function to control the degree of fiber variance in said apparatus.

2. The method according to claim 1, wherein the light source comprises a stroboscope.

3. A method for controlling the degree of fiber variations in paper sheet, comprising the steps of:

(1) generating a plurality of paper quality membership function curves for categorizing the quality of the paper into categories ranging from lowest to highest quality, the categories corresponding to formation factors of the paper, the formation factors of the paper being obtained by (a) picking up an image of transmitted light from a light source on an area of paper by a plurality of cameras with different visual fields, the cameras being arranged so that images of the transmitted light are picked up by the cameras concurrently in comparatively wide and narrow visual fields and are introduced to a display unit of an image processing computing element, there being provided means for changing the visual field introduced to the display unit;

(b) dividing the image of the transmitted light on the display unit into a predetermined size and number of windows, the windows comprising pixels;

(c) measuring the tone density of each pixel, and calculating the tone density of each window from the tone density of the pixels of which the window is comprised;

(d) calculating values chosen from at least one of the following:
    an average value of tone density and a primary variance of tone density of each window from the tone density of each pixel,
    an average value of the primary variance of tone density for all of the windows,
    a secondary variance of tone density for all of the windows, and
    a variance of average values of tone density of each window; and (e) using one of or at least two in combination of said values as a formation factor;

(f) changing the visual field transmitted to the display unit by said plurality of cameras and repeating the steps (a)-(e) so as to obtain a different formation factor corresponding to the different camera position;

(g) repeating step (f) one or more times so as to obtain a number of formation factors from which a paper quality membership function curve can be calculated:

(h) repeating steps (a)-(g) for a plurality of different paper sheets having highest to lowest quality so as to thereby obtain said plurality of paper quality membership function curves;

(2) generating a plurality of separate operation control membership function curves corresponding to operation factors comprising, respectively, changes of J/W ratio, changes in foil angle, and changes in deflector pushing degree, said changes being in response to each of the paper quality membership function curves generated in step (1), (3) obtaining a degree of matching at intersections of the paper quality membership function curves with each of the operation control membership curves, (4) for the control of each of said operation factors J/W ratio, foil angle, and deflector pushing degree, in sequence, (A) obtaining in correspondence to each of the matching degrees, results of the estimated changes of the operation factor from the respective operation control membership function curves, (B) overlapping and synthesizing results of the estimated change of the operation factor to generate final operation control membership functions providing a final estimated result of the change, (C) determining the actual change to be effected with regard to the operation factor based on the final operation control membership function, (D) adjusting the operation factor based on said determined actual change, and (E) repeating steps (A)-(D) for each of the remaining operation factors.

4. The method according to claim 3 wherein the operation control membership function is selected depending upon whether any difference between the formation factor of a previous control and the formation factor in a present control is positive or negative.

5. The method according to claim 3, wherein step (1) (f) comprises
  commensurate with the starting of measurement, observing the formation of the entire paper by lifting at least one camera along a rail to widen the visual field of the camera,
  gradually narrowing the visual field of the camera by moving the camera down along the rail as the formation is improved after starting the control by method, and
  lifting the camera up again to return to the initial large visual field for monitoring when the formation is substantially stabilized.

6. The method according to claim 5 wherein the range of change of control variables in J/W ratio, and in initial drainage and finishing drainage are initially set to large values for coarse control; and after the coarse control is completed, the range of changes of each of the control variables is set to smaller values so that fine control is performed in steps.

7. The method according to claim 3, wherein a plurality of cameras for changeover are arranged to have different distances from the paper; wherein step (1) (f) comprises at the starting of measurement, observing the formation of the entire paper by one of the cameras with the widest visual field;

sequentially changing over to one of the cameras with a narrower visual field as the formation is improved after starting the control by said method; and changing over to the camera with the widest visual field again for monitoring when the formation is substantially stabilized.

8. The method according to claim 7 wherein monitoring is started in a status where the formation is being stabilized in the control of the last stage.

9. The method according to claim 3, further comprising the step of frequency-analyzing the density of image in the lateral direction to determine whether formation is pulling or pushing; and, in the case of pulling formation, the J/W ratio is increased and in the case of pushing formation, the J/W ratio is decreased.

10. The method of claim 3, wherein the foil angle is optimized simultaneously for a plurality of foils for initial drainage control, and wherein the deflector pushing degree is optimized simultaneously for a plurality of deflectors for finishing drainage control.

* * * * *